US009486356B2

(12) United States Patent
Agnew et al.

(10) Patent No.: US 9,486,356 B2
(45) Date of Patent: Nov. 8, 2016

(54) EYE DROPPER

(71) Applicants: William Agnew, Salisbury, MD (US); Thomas Dunlap, Purcellville, VA (US)

(72) Inventors: William Agnew, Salisbury, MD (US); Thomas Dunlap, Purcellville, VA (US)

(73) Assignee: Wellspring Oculus LLC, Leesburg, VA (US)

( * ) Notice: Subject to any disclaimer, the term of this patent is extended or adjusted under 35 U.S.C. 154(b) by 170 days.

(21) Appl. No.: 14/269,983

(22) Filed: May 5, 2014

(65) Prior Publication Data

US 2015/0313757 A1 Nov. 5, 2015

(51) Int. Cl.
*A61M 35/00* (2006.01)
*A61F 9/00* (2006.01)

(52) U.S. Cl.
CPC .......... *A61F 9/0008* (2013.01); *A61F 9/0026* (2013.01)

(58) Field of Classification Search
CPC ............................ A61F 9/0008; A61F 9/0026
USPC ........................................ 604/295, 300, 302
See application file for complete search history.

(56) References Cited

U.S. PATENT DOCUMENTS

| | | | | |
|---|---|---|---|---|
| 2,722,216 A | | 11/1955 | Robbins | |
| 3,521,636 A | * | 7/1970 | Weckesser | A61F 9/0026 604/302 |
| 3,756,478 A | * | 9/1973 | Podell | B65D 47/18 222/211 |
| 4,002,168 A | * | 1/1977 | Petterson | A61F 9/0008 222/421 |
| 4,134,403 A | * | 1/1979 | Johnsen | A61F 9/0026 222/192 |
| 4,257,417 A | * | 3/1981 | Gibilisco | A61F 9/0026 604/302 |
| 4,392,590 A | * | 7/1983 | Hofmann-Igl | A61F 9/0026 222/174 |
| 5,069,675 A | * | 12/1991 | Menchel | A61F 9/0008 222/206 |
| 6,041,978 A | * | 3/2000 | Hagele | A61F 9/0008 222/211 |
| 6,197,008 B1 | | 3/2001 | Hagele | |
| 6,595,970 B1 | * | 7/2003 | Davidian | A61F 9/0026 604/298 |
| 6,632,202 B1 | | 10/2003 | Hagele | |
| 7,527,613 B2 | * | 5/2009 | Gaynes | A61F 9/0008 604/295 |
| 7,846,140 B2 | * | 12/2010 | Hagele | A61F 9/0008 604/295 |
| 9,033,941 B2 | * | 5/2015 | Rehkemper | A61F 9/0026 604/295 |
| 2005/0043693 A1 | | 2/2005 | Infantolino | |
| 2005/0288640 A1 | * | 12/2005 | Cress | A61M 35/003 604/300 |
| 2006/0069358 A1 | | 3/2006 | Gerondale | |
| 2007/0055208 A1 | * | 3/2007 | Berger | A61F 9/0026 604/295 |
| 2014/0350492 A1 | * | 11/2014 | Rojas Escalante | A61F 9/0008 604/295 |

* cited by examiner

*Primary Examiner* — Susan Su

(74) *Attorney, Agent, or Firm* — Dunlap Bennett & Ludwig PLLC

(57) ABSTRACT

An eye dropper bottle including a notch for resting on the bridge of a nose is provided. The eye dropper bottle may include a curved neck with a nozzle. The nozzle may be oriented at an angle relative to the bottle. A user may place the notch on the bridge of the nose so that the nozzle is disposed over the eye. The user may then squeeze the bottle to dispense the liquid into the eye.

13 Claims, 2 Drawing Sheets

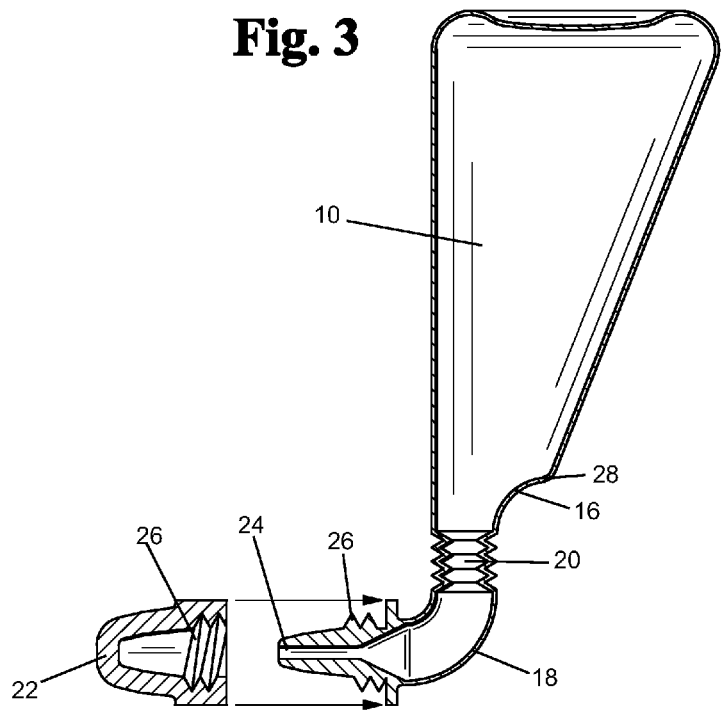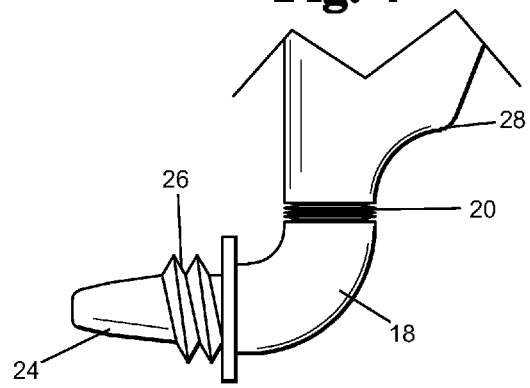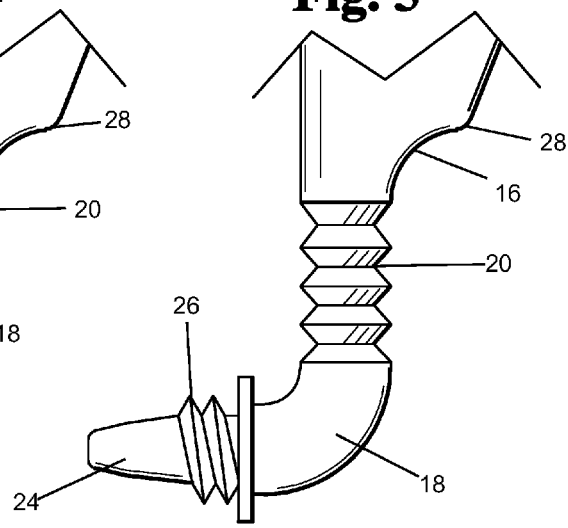

EYE DROPPER

BACKGROUND OF THE INVENTION

The present invention relates to an eye dropper and, more particularly, to an eye dropper having a notch to rest on the bridge of the nose.

Currently, eye droppers include a bottle to hold a solution, and a nozzle to drop the solution into a user's eye. For some individuals, dropping the solution into the eye may be difficult. For example, the user may not know where to effectively place the nozzle to deliver the appropriate drop. Further, the user may rapidly blink from discomfort and therefore may not focus on holding the bottle in the proper position.

As can be seen, there is a need for an improved eye dropper bottle to effectively deliver eye drops.

SUMMARY OF THE INVENTION

In one aspect of the present invention, an eyedropper comprises: a bottle comprising a first end and a second end, wherein the bottle comprises an internal portion formed to store a liquid; a notch formed in the bottle and configured to rest on a bridge of a nose; and a neck extending from the second end of the bottle and comprising a nozzle, wherein the nozzle is oriented at an angle relative to the bottle.

In another aspect of the present invention, a method of dropping a liquid into an eye comprises: providing a bottle having a liquid within, wherein the bottle comprises a notch and a neck, wherein the neck extends from the bottle and comprises a nozzle oriented at an angle relative to the bottle; resting the notch on a bridge of a nose, thereby orienting the nozzle over an eye; and squeezing the bottle and thereby squeezing the liquid out of the nozzle and into the eye.

These and other features, aspects and advantages of the present invention will become better understood with reference to the following drawings, description and claims.

BRIEF DESCRIPTION OF THE DRAWINGS

FIG. 3 is a cross-sectional view of FIG. 2;

FIG. 4 is a detail side view of the adjustable portion of the neck of FIG. 1 in a retracted configuration; and FIG. 5 is a detail side view of the adjustable portion of the neck of FIG. 1 in an extended configuration.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides an eye dropper bottle including a notch for resting on the bridge of a nose. The eye dropper bottle may include a curved neck with a nozzle at the end. The nozzle may be oriented at an angle relative to the bottle. A user may place the notch on the bridge of the nose so that the nozzle is disposed over the eye. The user may then squeeze the bottle to dispense the liquid into the eye.

The present invention includes an easy to use eye dropper bottle. The eye dropper bottle may include a notch formed to fit on a bridge of a user's nose. The eye dropper may further include an adjustable neck. Therefore, the present invention allows the user to easily balance the bottle on the bridge of the nose, and thereby align the dropper tip or nozzle with the eye. Further, the neck may be adjustable to suite different users. Therefore, the present invention allows for easy balance and targeted dropping.

Figure 1:
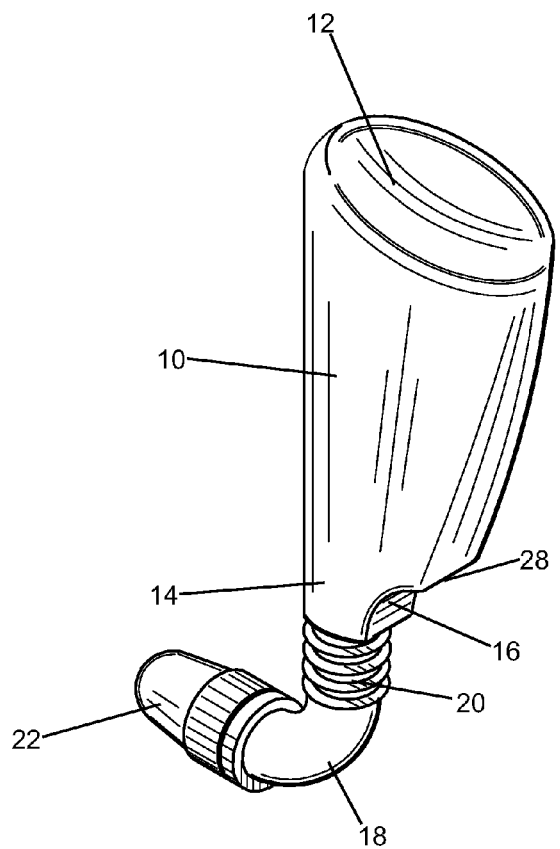
FIG. 1 is a perspective view of the present invention.
Figure 2:
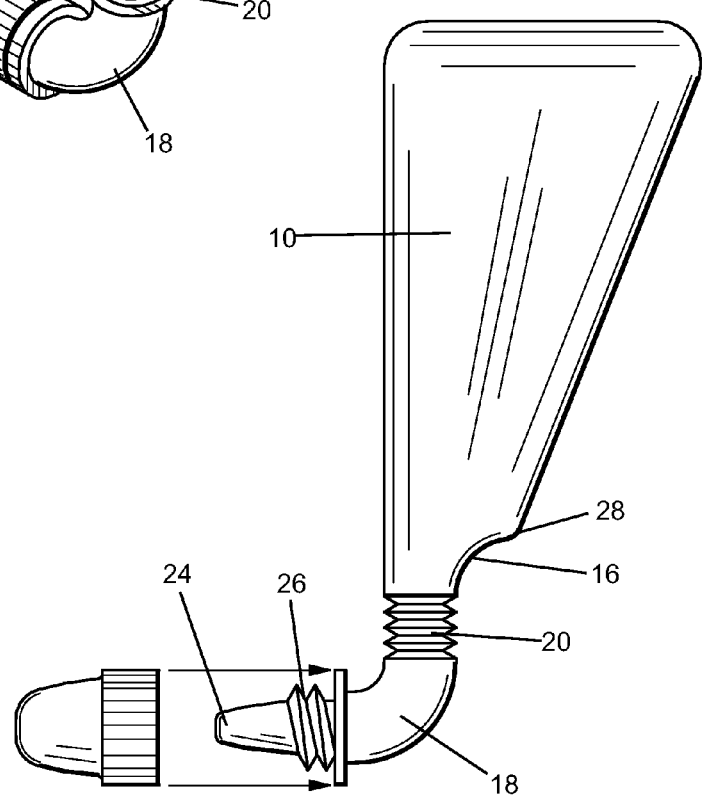
FIG. 2 is an exploded side view of the present invention illustrating the cap of FIG. 1 removed from the nozzle.

Referring to FIGS. 1 through 5, the present invention includes an eyedropper bottle 10. The bottle 10 includes a first end 12 and a second end 14 with an internal portion formed to store a liquid solution. The bottle 10 of the present invention includes a notch 16 configured to rest on a bridge of a nose. A neck 18 may extend from the second end 14 of the bottle 10. The neck 18 includes a nozzle 24 which is oriented at an angle relative to the bottle 10. Therefore, a user may place the notch 16 on the bridge of the nose and apply drops from the bottle 10 directly to the eye of the user.

The bottle 10 of the present invention may include a squeezable dropper bottle 10 that is used for dispensing and storing liquid solutions. The squeezable dropper bottle 10 may be made of a flexible polymer, such as a plastic. Squeezing the bottle 10 may control the liquid dripping from the nozzle 24. The first end 12 of the bottle 10 may include a ridge formed around the perimeter to support the bottle 10 in an upright position when placed on a flat surface.

The notch 16 of the present invention may include a channel formed in the surface of the bottle 10. In certain embodiments, the notch 16 may begin at the neck 18 and may curve downward towards the first end 12 of the bottle 10. The notch 16 may curve to an end at a side of the bottle 10. In certain embodiments, the notch 16 may end at a ridge 28 so that the bridge of the nose is properly secured within. In certain embodiments, a non-slip polymer layer may line the notch 16 to prevent the bridge of the nose from slipping out of the notch 16.

In certain embodiments, the neck 18 of the present invention may curve, and thereby orient the nozzle 24 at an angle relative to the bottle 10. The neck 18 may be curved away from the notch 16 so that the nozzle 24 is positioned over the eye when the notch 16 is placed on the bridge of the nose. In certain embodiments, the neck 18 may curve along a 90 degree angle so that the nozzle 24 is substantially perpendicular relative to the bottle 10.

In certain embodiments, the present invention may include an adjustable portion 20 on the neck 18. The adjustable portion 20 may allow a user to adjust the neck 18 so that the nozzle 24 is properly positioned above the eye. The adjustable portion 20 may adjust the length of the neck 18. As illustrated in the Figures, the adjustable portion 20 may include an accordion. The accordion includes an extended configuration and a retracted configuration. The extended configuration increases the length of the neck 18, and the retracted configuration decreases the length of the neck 18.

In certain embodiments, the adjustable portion 20, such as the accordion, may be located anywhere along the neck 18. As illustrated in the Figures, the adjustable portion 20 may be near the second end 14 of the bottle 10. However, the adjustable portion 20 may also be along the bend of the neck 18, near the nozzle 24, or a combination thereof. Therefore, the neck 18 may be adjustable vertically and/or horizontally in length.

The present invention may further include a cap 22 that covers the nozzle 24 when not in use. The cap 22 may preserve the liquid within bottle 10 and may further prevent the liquid from spilling from the bottle 10. In certain embodiments, the cap 22 may include a threaded portion 26 that mates with a threaded portion 26 along the neck 18. Therefore, the cap 22 may easily be removed and attached. However, the cap 22 may be attached using other devices, such as snap locks, and the like.

The present invention may further include a method of dropping a liquid into an eye. The method may include using the bottle mentioned above. The notch may rest on the bridge of the nose, thereby orienting the nozzle over the eye of a user. The bottle may then be squeezed to squeeze the liquid out of the nozzle and into the eye. When the neck of the bottle includes the adjustable portion, the user may first adjust the length of the neck prior to resting the notch on the bridge of the nose so that the nozzle may be properly placed over the eye.

It should be understood, of course, that the foregoing relates to exemplary embodiments of the invention and that modifications may be made without departing from the spirit and scope of the invention as set forth in the following claims.

What is claimed is:

1. An eyedropper comprising:
   a bottle comprising a first end and a second end, wherein the bottle comprises an internal portion formed to store a liquid;
   a notch formed in the second end of the bottle and configured to rest on a bridge of a nose; and
   a neck extending from the second end of the bottle and comprising a nozzle, wherein the neck curves and thereby orients the nozzle at the angle relative to the bottle.

2. The eyedropper of claim 1, wherein the neck is curved away from the notch.

3. The eyedropper of claim 2, wherein the neck curves along a 90 degree angle, and thereby the nozzle is substantially perpendicular to the bottle.

4. The eyedropper of claim 1, wherein the neck further comprises an adjustable portion.

5. The eyedropper of claim 4, wherein the adjustable portion is an accordion comprising an extended configuration and a retracted configuration, wherein the extended configuration increases the length of the neck, and the retracted configuration decreases the length of the neck.

6. The eyedropper of claim 1, further comprising a cap releasably attachable to the nozzle.

7. The eyedropper of claim 6, wherein the cap is releasably attachable to the nozzle by threaded portions.

8. The eyedropper of claim 1, wherein the notch begins at the neck and curves towards the first end and ends at a ridge on a side of the bottle.

9. A method of dropping a liquid into an eye comprising:
   providing a bottle having a liquid within, wherein the bottle comprises a notch and a neck, wherein the neck extends from the bottle and comprises a nozzle oriented at an angle relative to the bottle;
   resting the notch on a bridge of a nose, thereby orienting the nozzle over an eye; and
   squeezing the bottle and thereby squeezing the liquid out of the nozzle and into the eye.

10. The method of claim 9, wherein the neck comprises an adjustable portion.

11. The method of claim 10, further comprising the step of adjusting the length of the neck.

12. The method of claim 9, wherein the nozzle is substantially perpendicular relative to the bottle.

13. The method of claim 9, wherein the notch begins at the neck and curves towards the first end and ends at a ridge on a side of the bottle.

* * * * *